United States Patent
Sivovolenko

(10) Patent No.: US 9,292,966 B2
(45) Date of Patent: *Mar. 22, 2016

(54) METHOD AND SYSTEM FOR IMPROVED OPTICAL MODELING OF GEMSTONES

(71) Applicant: Ideal-Scope PTY. LTD., Canterbury, Victoria (AU)

(72) Inventor: Sergey Borisovich Sivovolenko, Tampere (FI)

(73) Assignee: Ideal-Scope Pty. Ltd., Canterbury (AU)

( * ) Notice: Subject to any disclaimer, the term of this patent is extended or adjusted under 35 U.S.C. 154(b) by 0 days.

This patent is subject to a terminal disclaimer.

(21) Appl. No.: 14/106,473

(22) Filed: Dec. 13, 2013

(65) Prior Publication Data

US 2014/0107986 A1    Apr. 17, 2014

Related U.S. Application Data

(63) Continuation of application No. 12/743,559, filed as application No. PCT/EP2008/063307 on Oct. 6, 2008, now Pat. No. 8,639,479.

(30) Foreign Application Priority Data

Nov. 27, 2007 (AU) ................................ 2007906469

(51) Int. Cl.
*G06F 17/50* (2006.01)
*G06T 17/10* (2006.01)
(Continued)

(52) U.S. Cl.
CPC ............... *G06T 17/10* (2013.01); *G01N 21/87* (2013.01); *G01N 21/88* (2013.01); *G06T 17/20* (2013.01); *A44C 17/001* (2013.01); *G01N 33/381* (2013.01); *G06F 17/50* (2013.01)

(58) Field of Classification Search
CPC ..... G01N 21/87; G01N 33/381; G01N 21/88; A44C 17/001; A44C 27/00; G06F 17/50; G06F 17/5009; G06F 17/5004; G06T 17/10; G06T 17/20

USPC .............................. 700/98; 703/1, 2; 345/420
See application file for complete search history.

(56) References Cited

U.S. PATENT DOCUMENTS 5,966,673 A * 10/1999 Shannon, Sr. ................... 702/35
6,239,867 B1    5/2001 Aggarwal
(Continued)

FOREIGN PATENT DOCUMENTS

EP    2225731 B1    9/2010
GB    2406252 A     3/2005
(Continued)

OTHER PUBLICATIONS

F O. Bartell ; E. L. Dereniak ; W. L. Wolfe; The Theory and Measurement of Bidirectional Reflectance Distribution Function (BRDF) and Bidirectional Transmittance Distribution Function (BTDF). Proc. SPIE 0257, Radiation Scattering in Optical Systems, 154 (Mar. 3, 1981).*

(Continued)

*Primary Examiner* — Aniss Chad
*Assistant Examiner* — Cedric D Johnson
(74) *Attorney, Agent, or Firm* — Bret E. Field; Bozicevic, Field & Francis LLP

(57) ABSTRACT

Methods of constructing a virtual model of a gemstone are provided. Aspects of the methods include performing measurements of the gemstone to construct a three-dimensional (3D) model of an exterior surface of the gemstone; identifying one or more visible inclusions within an interior volume of the gemstone; capturing at least one image of the inclusion; using the at least one image to determine relevant optical characteristics of the inclusion; and constructing a 3D virtual model of the inclusion.

17 Claims, 4 Drawing Sheets

(51) Int. Cl.
*G01N 21/88* (2006.01)
*G01N 21/87* (2006.01)
*G06T 17/20* (2006.01)
*A44C 17/00* (2006.01)
*G01N 33/38* (2006.01)

(56) References Cited

U.S. PATENT DOCUMENTS

| | | |
|---|---|---|
| 2003/0223054 A1* | 12/2003 | Warwick .................... 356/30 |
| 2004/0051861 A1 | 3/2004 | Bray |
| 2005/0187831 A1* | 8/2005 | Gershburg et al. ............ 705/27 |
| 2006/0062446 A1* | 3/2006 | Porat ............................ 382/154 |
| 2006/0190292 A1 | 8/2006 | Reinitz et al. |
| 2007/0036921 A1* | 2/2007 | Twitchen et al. ............. 428/15 |
| 2007/0067178 A1 | 3/2007 | Reinitz et al. |
| 2007/0157667 A1* | 7/2007 | Maltezos ............... A44C 17/00 63/32 |
| 2008/0231833 A1 | 9/2008 | Shlezinger et al. |

FOREIGN PATENT DOCUMENTS

| | | |
|---|---|---|
| WO | WO 03/099054 A2 | 12/2003 |
| WO | 2005048764 A1 | 6/2005 |
| WO | WO 2005/052540 A2 | 6/2005 |
| WO | WO 2005048764 A1 * | 6/2005 |
| WO | WO 2007/023444 A2 | 3/2007 |
| WO | WO 2009/068354 A1 | 6/2009 |

OTHER PUBLICATIONS

Feature analysis of granted claims 1 and 10 of EP 2225731 B1.
Print-out of YouTube page corresponding to Citation No. 2 (i.e. http://www.youtube.com/watch?v=Ybm3mMDqTOc).

* cited by examiner

METHOD AND SYSTEM FOR IMPROVED OPTICAL MODELING OF GEMSTONES

This application is a continuation application of U.S application Ser. No. 12/743,559 filed on May 18, 2010 and now issued as U.S. Pat. No. 8,639,479; which application is a 371 of PCT/EP2008/063307 filed on Oct. 6, 2008; which application claims priority to Australian Application No. 2007906469 filed on Nov. 27, 2007; the disclosures of which applications are herein incorporated by reference.

FIELD OF THE INVENTION

The present invention relates to the evaluation of gemstones, and more particularly to improved computer modeling of gemstones, and especially modeling of internal flaws (inclusions). Potential applications of the invention include, but are not limited to: modeling and visualisation of rough (uncut) gemstones; planning for cutting of rough gemstones; modeling and visualisation of cut/polished gemstones, either as proposed to be cut from an uncut stone, or of existing cut-and-polished stone; computerised clarity grading of proposed or existing cut/polished stones; and assessment of gemstone value. Embodiments of the invention are described herein with particular reference to the evaluation and computer modeling of diamonds, but it will be appreciated that the invention is also applicable to the modeling and evaluation of other types of precious and semi-precious gemstones.

BACKGROUND OF THE INVENTION

The value of a cut diamond is substantially determined by the so-called "4-Cs": Carat, Colour, Clarity and Cut. Of these, carat and colour are substantially objective characteristics that may be assigned specific values in a largely uncontentious manner. The carat value is simply the weight of the diamond, wherein one carat is equal to 200 milligrams. Colour, in terms of both hue and transparency, may also easily be measured objectively, although the results of such measurement are somewhat dependent upon lighting conditions. Most diamonds used as gemstones are substantially transparent with little tint (known as "white diamonds"), however the most common impurity, nitrogen, causes a yellow/brown tint that is present, to some degree, in almost all white diamonds. The most widely-used colour rating system is that of the Gemmological Institute of America (GIA), which assigns a grade from D (colourless) to Z (bright yellow colouration) to nominally white diamonds. Generally, less colouration is more desirable, although diamonds of hues other than yellow/brown, such as pink or blue diamonds, may be more valuable than white diamonds, due to their rarity and/or level of market interest. In any case, assessing diamond hue against colour standards, and transparency in terms of light absorption, presents little practical difficulty.

Clarity and cut, on the other hand, influence the visual appearance of gemstones in a relatively complex manner. Indeed, these characteristics exhibit complex interactions with one another, as well as with lighting, viewing position, and so forth. It has therefore proven far more difficult to arrive at broadly accepted objective measures of clarity and cut, and the measures that do exist do not always accord closely with the subjective beauty of cut gemstones, as assessed by consumers, under a range of everyday lighting and viewing conditions.

Gemstone clarity, in particular, is a quality relating to the existence and visual appearance of internal flaws often called "inclusions", or "internal characteristics". Clarity is also affected by surface defects, or blemishes. There are various causes of inclusions, which may be, for example, crystals of a foreign material, another crystal of the gemstone itself, or imperfections such as cracks which may appear whitish or cloudy. The clarity of a gemstone, such as a diamond, will depend upon the number, size, colour, location, orientation and visibility of inclusions.

The most widely used clarity grading scales are those of the GIA and the Hoge Raad voor Diamant or Diamond High Council (HRD), according to which clarity is measured under 10-times magnification with specified "dark field" illumination. This basically involves illuminating the base of the stone from the side, and observing the resulting appearance of the stone from the top under 10-times magnification. The GIA diamond grading scale provides a total of 11 grades in six categories. The categories and grades are: flawless (FL), internally flawless (IF); very very slightly included (VVS1, VVS2); very slightly included (VS1, VS2); slightly included (SI1, SI2); and included (I1, I2, I3). Diamond graders are trained to assign grades from the GIA scale in a consistent manner.

As noted above, complex interactions exist between clarity and cut. In particular, by identifying inclusions within a rough (uncut) gemstone, it is possible, in principle, to plan the cutting of the gemstone in such a manner as to minimise the impact of those inclusions upon the clarity of the final cut and polished stone. This is, however, not a trivial matter. Planning is accordingly one of the most valuable skills in the diamond industry, with rough stones being evaluated from an economic perspective, with a view to maximising the value and saleability of diamonds cut from a rough stone. All else being equal, larger (ie higher carat) diamonds are more valuable. Accordingly, it is generally desirable to cut the largest stones possible from the rough, assuming that this can be done without causing an unacceptable reduction in the clarity of the resulting stone.

Modern diamond planning is facilitated by sophisticated electronic and computerised tools. Scanning devices, often incorporating digital imaging and laser ranging technologies, are used to capture a three-dimensional (3D) computer model of the rough stone prior to cutting. At this stage, images of inclusions may also be captured, and their relative location within the stone estimated. Computer software tools then assist the planner in placing proposed cut stones within the three-dimensional model of the rough stone, and assessing their potential value, prior to the commencement of any actual cutting.

However, there remain considerable opportunities for further improvements to be made in the tools available to assist in the planning and evaluation of gemstones. As noted above, clarity grading is based upon visual appearance, under 10-times magnification and specified lighting and viewing conditions. It should be appreciated that the actual visual appearance of a gemstone under these conditions does not depend only upon the number and/or types of inclusions. In particular, the visual appearance also depends upon the location and orientation of the inclusions relative to the facets of the cut stone. For example, a thin crack viewed edge-on may be barely visible, whereas the same crack viewed side-on may substantially compromise the clarity of the cut stone. Such considerations are significantly complicated by the reflection and refraction of light at facets of the cut gemstone. In particular, the facets of a diamond are designed to act as tiny mirrors, which reflect light back up towards the surface of the diamond, in order to enhance its visual appearance. However, this mirror effect may also act to "multiply" inclusions, so that they may appear more numerous than they really are, and furthermore so that they may be visible, in reflection, from angles other than that directly presented to the viewing position.

Taking all of these complex factors into account, planning is not simply a matter of identifying an optimum compromise between size of a cut stone, and number of inclusions. The more sophisticated software tools therefore endeavour to provide the user with a more accurate representation of the visual appearance of the cut stone, taking into account the optical effects such as reflection and refraction of light. In the case of internal flaws, this may include placing wire-frame or false-colour representations of inclusions within a three-dimensional model such that the actual apparent number and size of the inclusions in the resulting stone may be evaluated on-screen. A further level of sophistication involves the capturing of images (eg photographs) of the inclusions, and placing these photographs on the visual images displayed to the user. While these approaches are useful, they remain inadequate because they fail accurately to show the actual visual appearance of the inclusions in the finished gemstone. Photographs, in particular, are limited to showing the inclusions as they appeared when photographed in the uncut stone, rather than under the specific lighting conditions applied for the purposes of clarity grading. Existing approaches have therefore proven inadequate for performing virtual clarity grading during the planning process, and this aspect of planing therefore remains an imprecise art relying upon the skill of the planner and, inevitably, some degree of intuition, or even luck.

In addition to planning for the purposes of optimising the clarity grade under the GIA grading conditions, it is often also desirable to assess the appearance of an existing cut gemstone, or a proposed gemstone to be cut from a rough stone, under a range of alternative lighting conditions. Notably, the lighting conditions used for GIA clarity grading are not the conditions under which the stone will be viewed by consumers in the showroom, or during normal wear of diamond jewellery. It may therefore be extremely useful to provide improved computer modeling of gemstones with internal flaws for the purposes of "virtual viewing" from a range of viewing positions, and under a variety of lighting conditions. Indeed, while ray-tracing software exists today that is capable of generating virtual images of three-dimensional objects under arbitrary viewing conditions, and even of animating such images, there is presently no effective way to obtain a sufficiently accurate model of a gemstone with internal flaws for use with such software.

It is therefore an object of the present invention to provide for improved virtual modeling of the visual appearance of rough and cut diamonds, for the purposes of, for example, evaluation, planning and virtual viewing.

SUMMARY OF THE INVENTION

In one aspect, the present invention provides a method according to claim 1.

Advantageously, embodiments of the inventive method mitigate the deficiencies of the prior art by providing for improved virtual optical modeling of inclusions within gemstones. In particular, whereas prior art methods rely upon wire-frame, false-colour, or other unrealistic models of inclusions, or alternatively superimpose images of inclusions captured from fixed locations under fixed lighting conditions, the present invention enables inclusions to be modelled in three dimensions in a manner which enables the subsequent generation of photorealistic three-dimensional images of the gemstone under arbitrary viewing conditions. This capability is believed to be unprecedented in the prior art.

A presently preferred embodiment of the method is set out in claim 2.

The gemstone may be, for example, a diamond. Furthermore, the gemstone may be either rough or cut/polished.

In preferred embodiments, the inventive method may be used to provide the user with a variety of different types of information relating to visual characteristics of the gemstone. In one exemplary embodiment, the visual characteristic is a predicted visual appearance of the gemstone as observed from a specified viewing position under specified lighting conditions. This may be achieved by using the gemstone virtual model in combination with known computerised optical ray-tracing techniques to generate one or more visual images of the gemstone as observed from any desired viewing position, under any desired lighting and viewing conditions.

For example, detailed models of ambient lighting conditions may be generated using High Dynamic Range Imaging (HDRI) technology. In one such approach, actual ambient conditions are recorded by capturing images of a reflective sphere within the desired ambient environment from multiple viewing locations, and using multiple exposure levels. Such images may be converted into an HDRI model of the environment, taking into account all light sources and objects within the environment, which may subsequently be used to generate visual images of the gemstone as it would appear if placed within the same environment.

Generated visual images of the gemstone may also take into account the viewing optics (including, if desired, optical characteristics of the human eye, as well as those of optical devices such as a loupe, microscope, photo camera, and so forth). Such models may utilise modulation transfer functions (MTFs) of components of the modelled imaging system, in order to simulate real observed image quality. Models may also take into account other imaging parameters such as magnification, distance between the imaging system (eg lens) and the gemstone, resolution, focal distance, aperture, depth of field, sharpness, and so forth.

Photorealistic three-dimensional images of the gemstone may be presented in a two-dimensional (ie monoscopic) form, in like manner to a conventional photograph. Alternatively, photorealistic three-dimensional images of the gemstone may be presented in a stereoscopic form, for example by generating and displaying dual images viewable using suitable 3D viewing apparatus, such as two-colour (eg green/red) glasses, polarising glasses, or liquid crystal shutter glasses.

Colour and/or brightness of generated visual images may be adapted as desired, for example in order to model variations in lighting conditions.

In the case that the gemstone is a rough stone, the visual characteristic may be the predicted visual appearance of a cut and/or polished gemstone proposed to be cut from the rough stone.

In a further exemplary embodiment, the information relating to a visual characteristic of the gemstone may be a clarity grade of a cut and polished gemstone. A clarity grade may be assigned by generating a photorealistic visual image of the cut and polished gemstone under the standard GIA lighting conditions, using computerised ray-tracing techniques, in order to produce a virtual image corresponding to the real image that would be observed during a standard clarity grading process. The clarity grade may then be assigned either by a trained grader, with reference to a displayed virtual image, or alternatively may be automated, by computer software assessing the size and visual appearance of each visible inclusion and applying clarity grading rules thereto, for example clarity grading rules defined by the HRD.

A preferred embodiment is set out in claim 7. Optical characteristics assigned to each inclusion may be values of parameters preferably selected from a list including colour, shade, fluorescence and transparency. In the case of a pinpoint, it may not be necessary to assign further parameter values, since the location of a point inclusion may be sufficient to fully model its optical properties via ray-tracing methods. Since a cloud is a cluster of pinpoints, additional parameter values may be similarly unnecessary. However, for accurate modeling it may be useful to assess the density of the cloud, which may be measured by its apparent shade and/or transparency. A crack may be assigned a shade (ie apparent brightness or darkness), and/or degree of transparency/translucency.

While prior art apparatus for scanning and/or viewing gemstones employs black and white imaging devices, colour imaging devices may be substituted in order to capture colour information of each inclusion. Such colour information may then be used to assign corresponding optical characteristics to the inclusion.

In the most general case however, optical characteristics assigned to each inclusion preferably include a texture map or "skin", representing the optical properties of the inclusion. Advantageously, the use of texture mapping enables extremely detailed modeling of the visual appearance of inclusions.

In accordance with embodiments of the present invention, texture includes colour or black and white imaging information of the inclusion, together with the mapping of such information to inclusion geometry. Accordingly, a texture map may consist of an array of pixels, each having properties such as colour, brightness, transparency, and so forth, along with a mapping of the array of pixels to corresponding coordinates on surfaces of the inclusion. Texture is preferably obtained by projection of calibrated inclusion images (eg digital photographs) to the inclusion geometry, with further merging of all projections (eg images captured from different viewing orientations) into a single texture map. Preferably, the texture is applied to the geometry of the inclusion during a visual imaging rendering process used to generate photorealistic three-dimensional images of the gemstone.

A bidirectional reflectance distribution function (BRDF) may be determined and assigned to each inclusion. As known to persons skilled in the relevant optical arts, the BRDF describes the ratio of light reflected from a surface as a function of light incident on the surface, taking into account the directions of incident and reflected light. The BRDF formalises the observation that colour shades and brightness of an object depend upon both the direction of illumination and the direction to the observer.

In various embodiments of the invention, different levels of operator input and intervention may be utilised in the course of constructing a virtual model of a gemstone. Preferably, each step in the method is either partly or wholly automated. User input may be obtained, for example, in order to identify each inclusion and/or to map out its 3D shape. User input may also be utilised to assign a type to each inclusion. Additionally, user input may be utilised to assign parameter values to each inclusion. However, it is particularly preferred that each step be automated as far as possible, in order to simplify the task of the operator, and to achieve maximum consistency and accuracy in the construction of the 3D virtual model.

In exemplary embodiments, the process of assigning optical characteristics to each inclusion, and in particular of creating a texture map of each inclusion, and assigning a BRDF to inclusion surfaces, may utilise an automated ray-tracing process. In particular, the step of capturing at least one image of each inclusion is preferably performed under controlled, and known, lighting conditions, which may be reproduced in the construction of corresponding computer-generated images using ray-tracing techniques. The computer-generated images may then be compared with the captured images of the inclusion, and assigned optical characteristics varied (for example by selection or variation of appropriate texture maps and BRDFs), and the computerised image generation repeated, until the computer-generated image closely matches the actual captured image. Advantageously, this approach provides an automated method for constructing accurate 3D virtual models of each inclusion.

For simple inclusions, such as pinpoints, needles or simple cracks, a single captured image may be sufficient to assign an inclusion type, assign any additional optical characteristics (eg parameter values, texture maps and/or BRDFs), and to construct a 3D virtual model of the inclusion. However, for more complex inclusions, such as irregularly-shaped clouds, it will be appreciated that the appearance of the inclusion may be quite different when viewed from different angles. Accordingly, in such cases a plurality of images of the inclusion may be captured from different viewpoints, and appropriate parameter values, such as texture and/or transparency, determined corresponding with the different viewpoints, and subsequently combined to generate the complete 3D virtual model of the inclusion. It may also be desirable to capture multiple images from each viewpoint under different lighting conditions, in order to improve estimation of BRDFs.

In preferred embodiments, the scanning apparatus includes a digital image-capturing device, such as a digital camera, and the instructions executable by the processor for capturing at least one image of each inclusion preferably include instructions directing the scanning apparatus to capture an image using the digital image-capturing device, and to transmit the captured image to the computer.

In preferred embodiments, the computer is further configured to display captured images to the user on the display device, and to generate and display virtual images of the gemstone on the display device. The user may provide input to the system, including input in relation to the identification of visible inclusions, the location of visible inclusions, the 3D shape of visible inclusions, inclusion type, and/or inclusion optical characteristics, via the one or more user input devices.

In particularly preferred embodiments, the computer is configured to generate and display photorealistic virtual images of the gemstone and/or of further stones cut from the gemstone, using the 3D virtual model of the gemstone. In particular, photorealistic images may be generated using ray-tracing methods. More particularly, preferred More embodiments of the system are able to generate images representing predicted visual appearance of the gemstone as observed from a specified viewing position under specified lighting conditions using computerised ray-tracing techniques. The generated visual images may be visual images of a rough gemstone, or may represent the predicted visual appearance of a cut and/or polished gemstone proposed to be cut from a rough stone. A skilled operator may be able to assess a clarity grading of a proposed cut and polished gemstone based upon the displayed visual images.

In some embodiments, the computer may further be configured to automatically assess a clarity grading of a proposed cut and polished gemstone by using ray-tracing methods to generate a visual image of the gemstone under standard clarity grading lighting conditions, and calculating a clarity grade by analysing the image and applying grading rules.

Further preferred features and advantages of the present invention will be apparent to those skilled in the art from the following description of preferred embodiments of the invention, which should not be considered to be limiting of the scope of the invention as defined in any of the preceding statements, or in the claims appended hereto.

BRIEF DESCRIPTION OF THE DRAWINGS

Preferred embodiments of the invention are described with reference to the accompanying drawings, wherein.

DETAILED DESCRIPTION OF PREFERRED EMBODIMENTS

Figure 1:
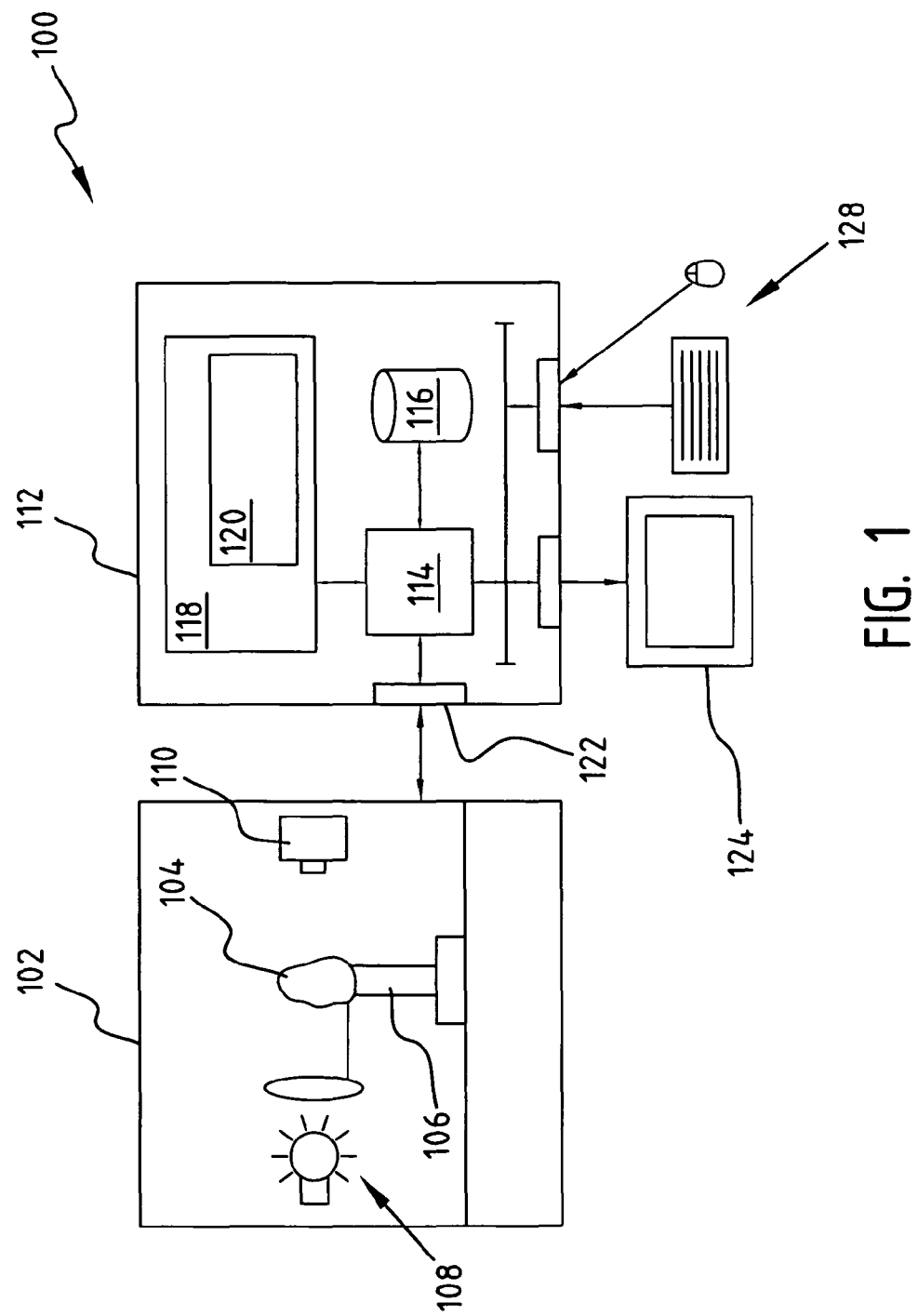
FIG. 1 is a schematic diagram of a system for generating a 3D optical model of a rough gemstone for evaluation according to a preferred embodiment of the present invention.

FIG. 1 illustrates schematically an exemplary system 100 embodying the present invention. The system 100 includes a gemstone-scanning apparatus 102 that is configured to perform measurements of a gemstone 104 in order to construct a three-dimensional (3D) model of an external surface of the gemstone. The scanning apparatus 102, according to embodiments of the present invention, is also able to capture information relevant to the identification, location, shape, and appearance of inclusions within the gemstone 104. In particular, the scanning apparatus includes a holder 106 upon which the gemstone 104 is fixed. The holder 106 is able to rotate and/or translate in order to reposition the gemstone 104 relative to light source 108 and imaging device 110.

In the exemplary embodiment shown in FIG. 1, the gemstone 104 is a rough diamond. However, embodiments of the invention may equally be used for modeling and evaluation of cut diamonds, and/or other gemstones.

The scanning apparatus 102 is generally configured to illuminate the gemstone 104 using a light source 108, and to capture images using imaging device 110, which is preferably a digital imaging device such as a digital camera. The scanning apparatus 102 may include additional light sources, for illuminating the gemstone 104 from a variety of different angles, for the purpose of capturing differently illuminated images using the digital imaging device 110. The light sources, including light source 108, may be computer or manually controlled, in order to optimise the identification, positioning, and visual analysis of inclusions within the gemstone 104. The capture of images of the gemstone 104, from a variety of different orientations, and possibly also under different lighting conditions, is the primary means by which the scanning apparatus 102 performs measurements of the gemstone 104.

While not shown in FIG. 1, the scanning apparatus may include additional components for performing measurements of the gemstone 104. For example, in some embodiments the scanning apparatus may also include laser-ranging devices (not shown) for scanning the surface of the gemstone 104 in order to better identify indentations and other surface features.

Various scanning apparatus generally suitable for use with the present invention are known in the prior art. These include apparatus described in U.S. Pat. No. 6,239,867 in the name of Lalit K. Aggarwal, issued on 29 May 2001, and UK patent application publication no. GB 2081439A in the name of Gersan Establishment, filed on 4 Jun. 1981 and published 17 Feb. 1982. More preferably, apparatus of the general type disclosed in European patent publication no. 1211503, in the names of Diamcad and the present inventor, may be utilised in embodiments of the present invention.

Scanning apparatus of the type disclosed in EP1211503 has an improved capability to identify the location of inclusions within the interior volume of the gemstone 104. The aforementioned documents are hereby incorporated by reference.

While it may be possible, in principle, to provide a single scanning apparatus 102 implementing all the required functionality of embodiments of the present invention, as a practical matter it is presently preferred that the functions of the apparatus 102 described herein actually be provided by two separate pieces of apparatus. As described in greater detail below, with reference to FIG. 2, methods according to embodiments of the present invention include separate steps of scanning an exterior surface of the gemstone 104, and imaging interior features (ie inclusions) of the gemstone 104. To the inventor's knowledge, there is presently no single apparatus 102 that is capable of performing both of these functions in an optimal manner. Products such as Helium™ provided by Octonus/Lexus, DiaScan™ provided by Sarin, are suitable for scanning exterior surfaces of rough and/or cut gemstones. Additionally, products such as M-Box™ with associated software Oxygen™, provided by Octonus/Lexus, which includes a binocular microscope, a digital camera, and a computer-controlled lighting arrangement, is designed for capturing images of internal features of gemstones. It will therefore be appreciated that the scope of the present invention encompasses the use of separate scanning and/or imaging apparatus for providing corresponding functionality in various embodiments. Furthermore, it will be understood that the term "scanning", as used herein, may encompass both exterior surface mapping, and interior imaging.

The scanning apparatus 102 is operatively connected to a computer 112 including a central processor 114, which is interfaced to storage devices, such as non-volatile storage device (eg hard-disk drive) 116 and volatile storage (eg random access memory) 118. The memory 118 relevantly contains program instructions 120 for execution by the processor 114, for carrying out various operations of the computer 112, including those related to the implementation of the present invention. As will be appreciated, the memory 118, and non-volatile storage 116, will also contain program instructions for execution by the processor 114 for performing a variety of other supporting functions, including various operating system functions of the computer 112.

The computer 112 further includes a peripheral interface 122, operatively associated with the processor 114, for communicating with the scanning apparatus 102. The peripheral interface 122 may be a standard interface, such as a parallel or serial (eg USB) port, or a proprietary interface.

The computer 112 is also interfaced to a display device 124, and user input devices 128 (eg keyboard and mouse), for interaction with a user or operator.

While FIG. 1 illustrates schematically a number of key components of an exemplary microprocessor-based apparatus for implementing embodiments of the present invention, it will be appreciated that the drawing does not show all peripherals, interfaces and components of the computer 112, which are well-known in the art but which are not relevant to the present discussion. The skilled person will, however, be familiar with the relevant further components making up a conventional computer system.

Figure 2:
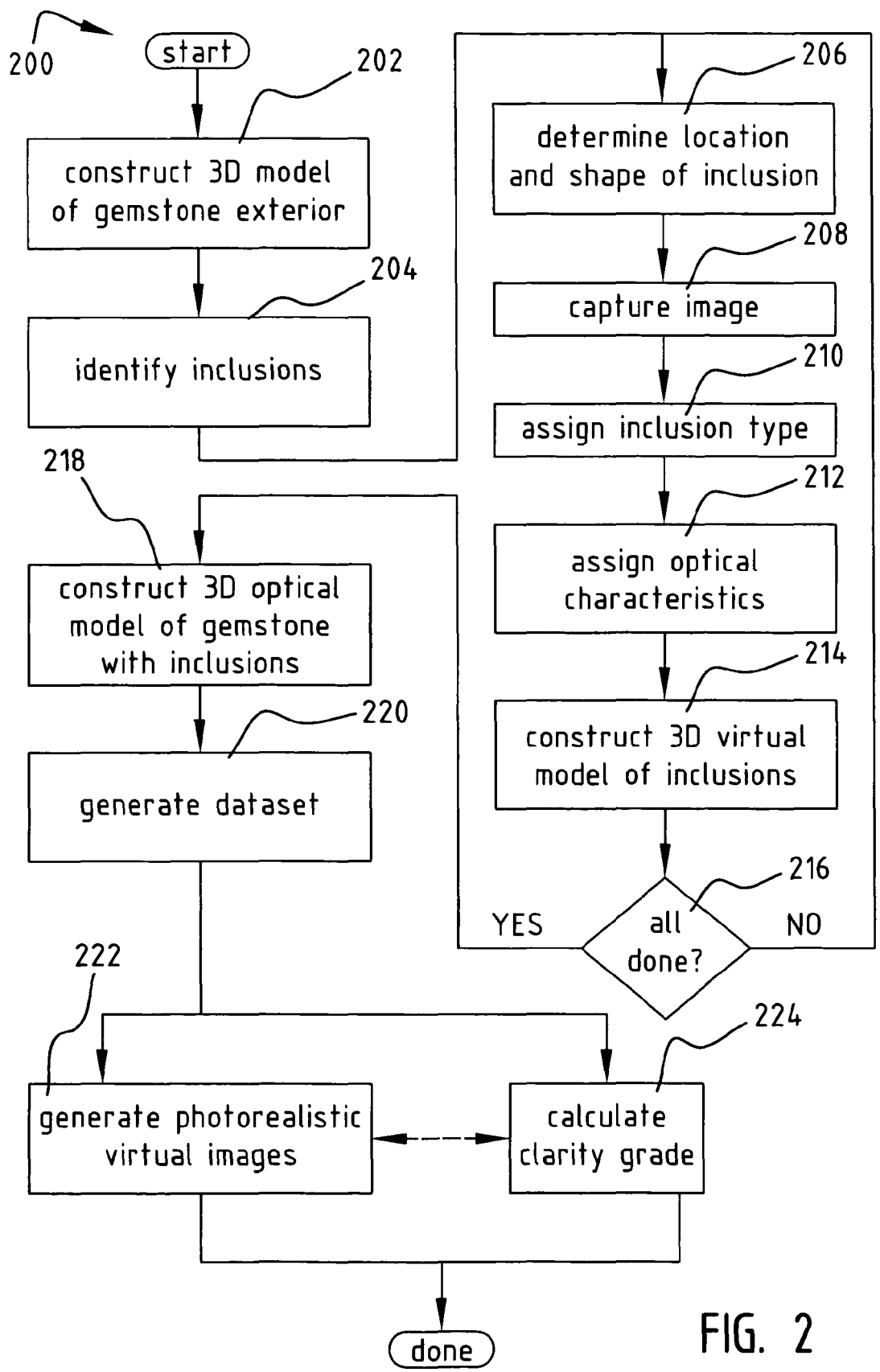
FIG. 2 is a flowchart illustrating a method of generating a 3D optical model of a gemstone utilising the system of FIG. 1.

FIG. 2 is a flowchart 200 which illustrates a method of generating a 3D optical model of a gemstone for evaluation according to preferred embodiments of the present invention. The method represented by flowchart 200 may be implemented using the system 100 illustrated in FIG. 1.

Each of the steps in a method according to preferred embodiments of the invention is described in greater detail below. While the flowchart 200 represents one particular sequence of operations, it will be appreciated that the specific order of steps is not limiting of the present invention, and it will be apparent from the following discussion that in various embodiments certain distinct steps represented in the flowchart 200 may be combined and/or reordered within the scope of the invention.

Construct 3D Model of Gemstone Exterior (Step 202)

The first step in accordance with an exemplary implementation of the invention is to perform measurements on the gemstone 104 to construct a 3D model of an exterior surface of the gemstone 104. As noted previously, scanning apparatus 102 capable of performing this function are known in the prior art. Typically, the gemstone, eg rough diamond 104, is rotated and/or translated on holder 106, successively illuminated using one or more sources of illumination, eg light source 108, and corresponding images of the diamond 104 captured using a digital imaging device 110. The images may be processed within the scanning apparatus 102, if the apparatus includes its own processor and associated software, or may be transferred to a separate computer 112 for processing, as in the exemplary embodiment 100 illustrated in FIG. 1.

Images of the diamond 104 captured at different rotational orientations relative to the digital imaging device 110 are processed, and in particular the processing preferably includes identifying an outline, or silhouette, of the diamond 104 at said varying rotational orientations. By combining the information from such multiple images, the system 100 is able to construct a 3D model of the exterior surface of the diamond 104. Additionally, as also noted previously, laser ranging devices may be included within the scanning apparatus 102, in order to identify and measure features such as indentations in the exterior surface of the diamond 104, which may not be readily visible in silhouette images captured by the digital imaging device 110.

Identifying Inclusions (Step 204)

The next step in the exemplary process is to identify inclusions within the diamond 104. Again, by illuminating the diamond and capturing images thereof, in particular under appropriate magnification, inclusions within the diamond 104 may be visible in the captured images. The process of identifying the shape and location of inclusions within the diamond 104 may be performed by an operator, or may be partly or wholly automated.

For example, images in which inclusions are visible may be displayed upon the display device 124. An operator may use the input devices 128 to identify and mark the location, shape and/or size of the visible inclusions. The computer 112 may then direct the scanning apparatus 102 to perform additional operations in order to identify the location and shape of the inclusions indicated by the operator, as described in greater detail below with reference to step 206.

Additionally, the operator may be able to use captured and displayed images, in combination with direct viewing of the diamond 104, in order to identify the shape and location of inclusions. For example, the operator may remove the diamond 104, complete with the holder 106 from the scanning apparatus 102, in order to perform a direct visual check of each inclusion, for example using a loupe, or other magnifying device, while also being able to view corresponding captured images on the display device 124 of the computer 112.

Alternatively, the computer 112 may be programmed to process images captured by the scanning apparatus 102, in order to identify likely locations of inclusions in an automated manner. Image processing may be used either to fully automate the process, or to present the operator with specific images on display device 124, for verification and/or optimisation of identification of inclusions detected via the image processing. Again, the operator may augment this process by direct visual inspection of the diamond 104, by removing it along with holder 106 from the apparatus 102 for viewing with a loupe or other magnfier.

Modeling Inclusions (Steps 206 to 216)

In accordance with the exemplary process illustrated by the flowchart 200, each identified inclusion is then subjected to further processing and modeling. The objective of the series of steps 206 to 214, which are applied to each inclusion in turn, is to construct a 3D virtual optical model of each inclusion. While the flowchart 200 indicates that all inclusions are first identified at step 204, and then each inclusion is subjected to further processing via the iterative sequence of steps 206 to 216, it will be readily appreciated that the steps 206 to 214 may be executed in relation to each inclusion in turn, as they are identified. That is, the step 204 may equivalently be incorporated within the loop defined in the flowchart 200 by steps 206 to 216. It will be understood that all such readily-apparent variations fall within the scope of the present invention.

Determine Location and Shape of Inclusion (Step 206)

As noted above, for each inclusion identified at step 204, it is necessary to establish the location of the inclusion within the diamond 104, as well as its three-dimensional shape.

Accurately identifying the location of features within the interior of a diamond is generally a relatively challenging problem. This is due to the particular optical properties of diamond, and especially due to its relatively high refractive index (approximately 2.42). The large index difference between the diamond material and the surrounding air leads to relatively high reflectivity for light incident at an angle upon interior surfaces, and also to relatively large degrees of refraction of light passing between the exterior and interior of the diamond, and vice versa. As a result of reflections and refraction, inclusions observed from the exterior of a diamond, eg 104, are generally not located within the interior volume of the diamond in the position in which they appear in externally captured images.

Various methods have been developed for more accurately locating inclusions observed within a gemstone, and preferred methods for use with the present invention are disclosed within the abovementioned document EP 1211503. An alternative, but less preferred approach, described in WO 2007/023444, in the name of Galatea Ltd and published on 1 Mar. 2007, involves immersing a diamond within a high refractive index liquid, in order to minimise the reflections and refraction that complicate locating inclusions within the diamond. This latter method suffers from a number of disadvantages, not least being the difficulty in handling, and common toxicity, of suitable high refractive index liquids. Additionally, immersing the diamond within a high refractive index liquid inevitably prevents accurate identification of the exterior surfaces. Accordingly, use of this technique in embodiments of the present invention would require that part of the process be performed without immersion, and a subsequent part with immersion, creating additional complications in implementation.

Following identification and location of each inclusion within the interior of the diamond 104, the three-dimensional shape of the inclusion is also determined. Again, this is a process that may be wholly or partly automated, or may rely more intensively upon operator intervention. For example, by presenting an operator with one or more images of the identified inclusion (eg from different viewing angles) on the display 124, the operator may use input devices 128 to mark out an exterior surface of the inclusion, thereby defining its shape. Alternatively, or additionally, the computer 112 may be programmed to perform processing of captured images of the inclusion, in order to automatically determine its three-dimensional shape. Intermediate implementations are also possible, for example where image processing is used to determine the 3D shape of each inclusion, and the operator is then presented with the results, for example as a wire-frame structure superimposed on one or more images of the inclusion on display device 124. The operator may then confirm the accuracy of the automatically generated three-dimensional shape information, or may be able to make modifications and adjustments as required. Confirming the accuracy of the three-dimensional shape information may include direct visual inspection of the diamond 104 by the operator, by removing the diamond 104 from the scanning apparatus 102, along with the holder 106, for direct viewing with a loupe or other magnifying device.

Determine Optical Characteristics of Inclusion (Steps 210 and 212)

After capturing an image of the inclusion in step 208, the next step in the processing of each inclusion is to determine relevant optical characteristics of each inclusion. In accordance with the exemplary embodiment of the invention, this step includes two sub-steps. First, the inclusion type is identified and assigned. Then, further characteristics of the inclusion are assigned, according to the type and visual appearance of the inclusion. These sub-steps are described in greater detail below.

Assign Inclusion Type (Step 210)

There are various types of inclusions which exist in gemstones such as diamonds, and each type may have different optical properties. For example, common inclusions within diamonds include pinpoints, clouds, cracks and needles. A "pinpoint" is an inclusion that appears as a tiny bright or dark point when viewed under magnification, typically caused by the growth of a tiny crystal within the gemstone. A "cloud" is generally a cluster of pinpoints. A "needle" is a long, thin inclusion, also typically a crystal growth within the gemstone. A "crack", also known as a "feather" or "gletz", is typically a small fracture within the gemstone. Cracks typically enclose small voids (eg vacuum) or air gaps within the gemstone, and therefore may have complex optical properties, resulting from multiple reflections and/or refractions of light.

Advantageously, by assigning a corresponding type to each identified inclusion, the most appropriate optical modeling techniques may be selected in order to represent the inclusion within the final virtual model of the diamond 104.

As with the previous steps, the assignment of an inclusion type to each inclusion may be based upon operator input, or may be wholly or partly automated. For example, the operator may be provided with a captured image of the inclusion on the display 124, along with a suitable user interface input element, such as a dropdown list, from which the appropriate type of inclusion may be selected based on the operator's observation of the captured image. Alternatively, the computer 112 may be programmed to identify at least some types of inclusion, on the basis of optical properties discernable from processing of captured images. The operator may be provided with the opportunity to verify and/or change an inclusion type automatically assigned by the computer 112.

Assign Optical Characteristics (Step 212)

As previously noted, different types of inclusion may have different optical properties. For example, cracks typically enclose a small void or air gap, and thus have a characteristic reflective and refractive properties. Pinpoints generally scatter light, and appear darker in front of a bright background (eg a facet from which light is reflected), and/or bright in front of a dark background (eg an unilluminated facet). A cloud is a collection of points of varying density, and thus exhibits a degree of translucency, as well as scattering and/or reflecting light.

Appropriate optical characteristics may be assigned to each inclusion, depending upon the inclusion type. The information required to assign suitable optical characteristics may vary greatly, depending upon the type of inclusion. In some cases, no additional optical characteristic information may be required. In other cases a great deal of additional information may be necessary in order to properly characterise an inclusion. Information, and relevant optical characteristics, may be captured and/or generated automatically, or may be provided by, or with the assistance of, operator input.

For example, an extremely small pinpoint may require no additional information to be captured. If information is required, a single captured image may be sufficient to fully characterise the inclusion, and also to locate the inclusion if the external surface through which it is viewed is flat (such as a facet of a cut diamond, or a purposefully faceted "window" of a rough stone). An automated process, in general, utilises images that have been captured under known lighting conditions, which can therefore be reproduced in a virtual space within the computer 112. That is, by generating a model of the inclusion within the computer memory 118, and executing appropriate ray-tracing algorithms using virtual light sources corresponding with the known lighting arrangement within the scanning apparatus 102, the appearance of the virtual inclusion may be compared with the appearance of the actual inclusion in the corresponding captured image. If the virtual and actual images are identical, or nearly identical, then it may be concluded that the correct optical characteristics of the inclusion have been assigned.

As noted above, for a pinpoint a single photo may suffice, in order to confirm the optical characteristics, or alternatively an accurate model may be generated based upon operator description of apparent colour and size under the controlled lighting conditions.

For a complex cloud, it may be necessary to capture images from a number of different orientations and/or using different light sources and/or different magnifications, since the cloud may have different optical properties when viewed from different positions, due to variations in shape and density. Again, operator input, such as apparent translucency or light transmittance, may be of use in assigning optical characteristics. In the most general case, however, it is desirable for the optical characteristics to be assigned in the form of texture maps, or "skins", and/or BRDFs. Texture maps and BRDFs are surface models which take into account the properties of surfaces, such as roughness, translucency (transmittance), reflectivity, and so forth. Appropriate texture maps may, in general, be determined using the method outlined above, ie by estimating an appropriate texture and then comparing a captured image with a corresponding virtual image generated by ray-tracing within the computer 112. The selected texture may subsequently be modified, as required, in order to improve the match between the virtual and actual images. For complex inclusions, textures may be generated for different portions of the inclusion, observed from different orientations, and then combined to create an overall texture map for the entire surface area of the inclusion.

Similarly, iterative methods may be used to estimate and assign BRDFs to identified inclusions. A BRDF (bidirectional reflectance distribution function) describes mathematically the ratio of light reflected from a surface to light incident on the surface, taking into account the directions of incidence and reflection. The BRDF formalises the widely observed fact that colour shade and/or brightness of a surface depend upon both the direction of illumination, and the direction from which the surface is observed. The BRDF captures this characteristic, such that the visual appearance of the surface may subsequently be rendered under different lighting and viewing conditions. According to preferred embodiments, images of the inclusion may be captured not only from different viewing orientations, but also under different lighting conditions. Corresponding virtual images may be generated by ray-tracing within the computer 112, and compared with the captured images, and an estimated BRDF may then be modified, as required, in order to improve the match between the virtual and actual images. The known geometry of each inclusion may be utilised to select the optimal lighting conditions for estimating a BRDF of a selected inclusion surface. For example, a crack may be intentionally oriented and lit in order to best show a surface thereof in high contrast against the background (eg a bright surface against a dark background, or vice versa). The selection of appropriate viewing orientations, and corresponding lighting conditions, may thus facilitate estimation of the BRDF. The same technique may also assist in the capture and assignment of texture maps to inclusion surfaces.

Additional optical properties of particular types of inclusion may also be taken into account in implementing appropriate models. For example, cracks are usually reflective under certain lighting conditions because they contain a void, or air, which results in optical phenomena such as Fresnel intensity losses. For a crack it may be necessary to use specially adapted light sources and positioning techniques in order to accurately determine transparency characteristics. All of the relevant optical effects can be modelled, given appropriate information regarding the inclusion type, dimensions and optical characteristics.

Construct 3D Virtual Model of Inclusions (Step 214)

Once all of the relevant information in relation to each inclusion has been established (ie location, three-dimensional shape, type of inclusion, optical characteristics) these are assembled at step 214 into a full 3D virtual model of the inclusion.

Iterate (Step 216)

At step 216, the processor checks whether all inclusions have been modelled, and if not proceeds to the next inclusion. Once all inclusions have been modelled, the process moves on to the next step.

Construction and Representation of 3D Optical Model (Steps 218 and 220)

At this point, the computer 112 has constructed a 3D model of the gemstone exterior, and 3D models of all visible inclusions within the interior volume of the gemstone.

These are combined at step 218 to construct a full 3D optical model of the diamond 104, with inclusions.

At step 220, a dataset corresponding with the 3D optical model is generated, and would typically be stored within memory 118, or non-volatile storage device 116, but additionally or alternatively may be transmitted, for example via a data communications network, to other locations for further processing. It is envisaged that the size of the dataset will be typically between 100 kilobytes and 300 kilobytes for diamonds with a number of small inclusions. Despite their relatively compact size, such datasets include all of the information necessary to generate photorealistic visual images of a gemstone under any desired viewing conditions. That is, files including these datasets embody a wealth of information that vastly exceeds that which would be contained in a single digital image of many megabytes. As will be appreciated, these compact files may be readily exchanged between interested parties, for example as email attachments, or as downloads over the Internet. This may enable, for example, the remote grading and/or valuation of diamonds, using generated photorealistic images, by experts and/or traders located anywhere in the world, without the need for direct access to the original gemstone itself.

Subsequent Analysis (Steps 222 and 224)

In accordance with preferred embodiments of the invention, once a full 3D optical model of the diamond 104 has been constructed, and a corresponding dataset generated, the model may be used for further analysis.

The typical operations that an operator may wish to perform include the generation of photorealistic virtual images (step 222) of the diamond 104 as viewed from selected angles/orientations, and under select lighting conditions. As known in the art, given a sufficiently detailed optical model, such as is produced by embodiments of the present invention, such photorealistic virtual images may be generated using known ray-tracing techniques.

Alternatively or additionally, the model may be used in order to automate the calculation of a clarity grade (step 224). This may be achieved by using ray-tracing methods to generate a photorealistic virtual image of the diamond 104 under standard GIA or HRD clarity grading lighting conditions, and at a standard 10-times magnification, and using the photorealistic virtual image to determine the clarity grade. Grading may be performed by an expert operator, or may be automated by implementing appropriate clarity grading rules in software for execution by the processor 114. Automated and manual grading may also be combined. For example, if automated grading produces a borderline or inconclusive result, one or more expert operators (graders and/or supervisors) may review the assigned grade.

In addition to facilitating automated clarity grading, embodiments of the present invention may also enable improved automated and/or semi-automated estimation of other desirable properties relating to cut quality of a gemstone, such as brilliance, fire, and scintillation. While existing software products, such as DiamCalc™ from Octonus, enable the calculation and visualisation of such properties, they are inherently limited by the inability of prior art methods to fully model the impact of inclusions. With embodiments of the present invention, placement, size and other factors of inclusions can be including within ray tracing computations (visual image rendering) to determine their effects on the quantification of such properties as light return and contrast (which can be combined to give a brilliance rating), fire (probability to see dispersion), scintillation, and other visual performance criteria. For example, clouds which may be difficult, or impossible, to see with the naked eye can nonetheless dull the light emanating from a diamond, and products embodying the present invention are able to fully account for such effects.

In preferred embodiments, where the diamond 104 is a rough stone, software also enables an operator to plan cut diamonds within the rough, and the further analysis may include generating photorealistic virtual images (step 222) and/or calculating clarity grades (step 224) in relation to the proposed cut diamonds. Accordingly, a more complete analysis and visualisation of proposed cut stones may be performed than is possible using existing systems, which do not accurately represent inclusions, without the need to perform any cutting of the rough diamond 104.

Illustrative Example of Operation and Interface

Figure 3:
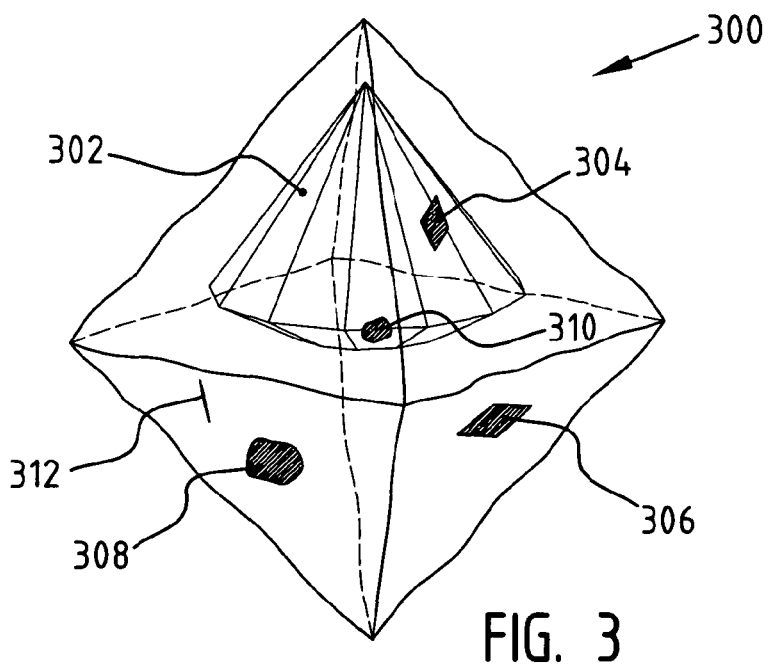
FIG. 3 illustrates schematically a 3D model of a gemstone according to an embodiment of the present invention.
Figure 4:
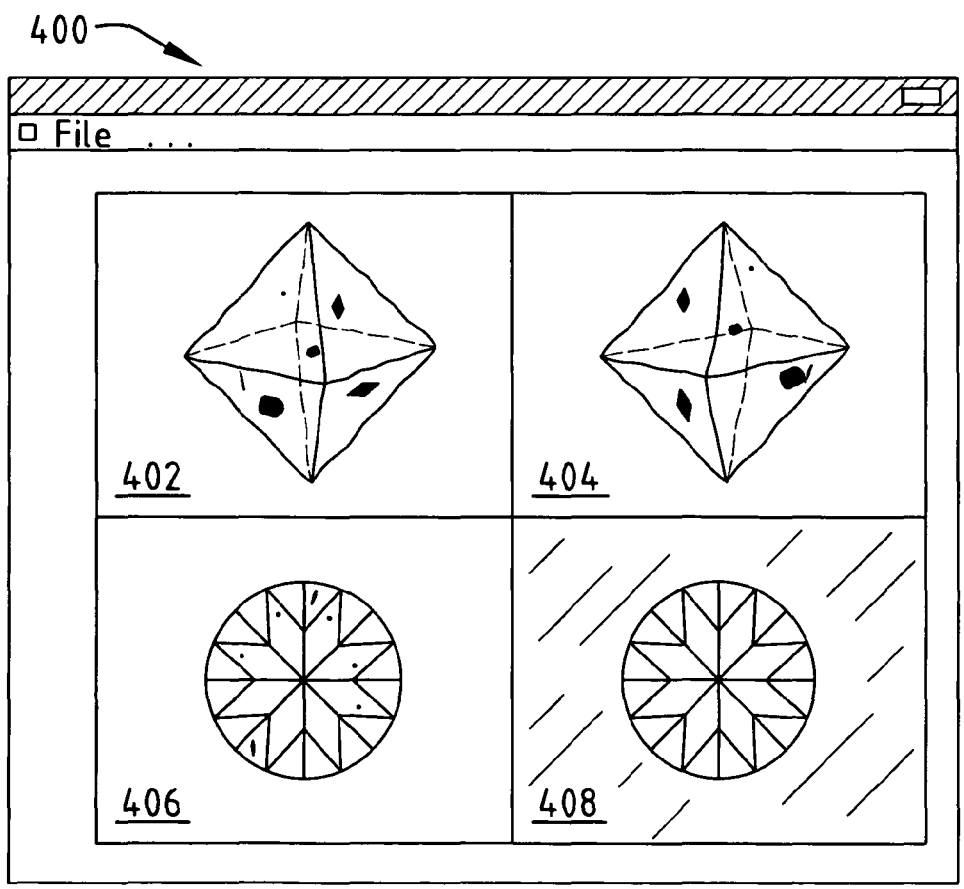
FIG. 4 illustrates schematically a display of a user interface to the system of FIG. 1.

FIGS. 3 and 4 serve to illustrate an exemplary application of the invention, and a corresponding operator interface. FIG. 3 is a schematic illustration of a 3D model 300 of a rough diamond, such as may be produced by embodiments of the invention. FIG. 4 illustrates an aspect of a user interface display 400, which enables visualisation of the model 300 by an operator.

The 3D model 300 includes a number of inclusions (302 to 312) that have been identified and modelled, for example using the above-described system/method. The inclusions may consist of, for example, pinpoints (302), cracks (304, 306), clouds (308, 310) and/or needles (312). Also shown within the rough diamond model 300 is a wire-frame image of a proposed cut diamond.

The operator is provided with a visual imaging interface 400, for example on display 124, through which it is possible to interact with, and visualise, the 3D model 300 in various ways. As shown, the interface 400 is a window including, amongst other elements omitted in FIG. 4 for the sake of clarity/simplicity, four viewing panes 402, 404, 406, 408. In the example shown, there is displayed in the top-left pane 402 a three dimensional image of the model 300. The top-right pane 404 displays a further image of the model 300, in a different orientation (ie rotated with respect to the first image 402). In bottom-left pane 406 there is displayed a wire-frame image of the proposed cut diamond, viewed from above the table of the cut stone, showing the various locations at which the inclusions within the interior volume of the diamond will be visible. The software uses ray-tracing techniques in each case to calculate the locations at which the inclusions will appear to be visible, taking into account the effects of reflections and refraction of light. As shown, the single pinpoint 302 is visible in five distinct apparent locations in the cut stone, due to reflection and refraction effects. The crack 304 is visible, edge-on, in two apparent locations.

Since the software "knows" which one of multiple images of a single inclusion is the directly viewed image, and which are the result of one or more reflections from facets of the diamond, it is possible to provide the operator with a feature to distinguish these different views. For example, the first (ie most direct, or singly refracted) view may be displayed in a different colour from the various reflected views. Alternatively, or additionally the software may enable the operator to "turn off" the generation of various reflected images, in order to assess the contribution of reflections to the appearance of the diamond, and reduction in clarity grade of the stone.

Due to the small size of the pinpoints, and the fact that the crack appears only edge-on (ie has minimum visible area) when viewed through the table of the cut diamond, the operator may suspect that the actual visible impact of these inclusions in the finished cut/polished stone may be minimal. To verify this hypothesis, a full photorealistic image corresponding with the wire-frame in pane 406 may be generated. In the interface 400, a photorealistic image is displayed in bottom-right pane 408. This image enables the operator to observe the actual expected appearance of the inclusions, for example under standard clarity grading conditions. This may enable the operator actually to assign a clarity grade of the proposed cut diamond, based upon the photorealistic image. Alternatively, automated clarity grading may be possible, based upon software processing of the photorealistic image using appropriate clarity grading rules.

Further, when showing the 3D model to the user, the limited depth of field (DOF) may be taken into account. When a grader is looking at an inclusion through a loop, depth of field limitations will affect the view the grader gets. To avoid the observer obtaining a worse view than would be seen under magnification, it is advantageous to include the typical depth of field limitations in the generation of the displayed image. This depth of field (DOF) can have a control to toggle up and down through the virtual gemstone. DOF here refers to the way you can focus through a lens and see all of the inclusions in a certain plane in focus, while just above and just below this plane will be out of focus. Further away from this field of view in the direction of the top or the bottom of a gemstone the inclusions will not be visible until you move the lens closer or further away.

In a normal digital rendering (not taking into account the DOF limitations) all the inclusions and their reflections (and facets) in a gem would be in perfect focus. If that is the case then a diamond with a slight inclusion can appear to be very bad and unsaleable. By adding a digital depth of field it becomes possible to see the gemstone the way a person does in reality with magnification.

A preferred viewer tool of the software for zooming in/out should take into account the DOF. More in particular, when a user zooms in the depth of field should become smaller (shallower).

Imaging of Cut Gemstones

While FIG. 1 illustrates an arrangement 100 for performing measurements upon a rough diamond 104, as has previously been noted embodiments of the present invention are equally applicable to measurement and modeling of cut gemstones. In many cases there may be no especially preferred orientation of a rough gemstone 104 upon a holder 106, since the uncut external surface has no particularly preferred viewing direction. However, this may not be so in the case of a cut gemstone, such as an ideal cut diamond.

Figure 5:
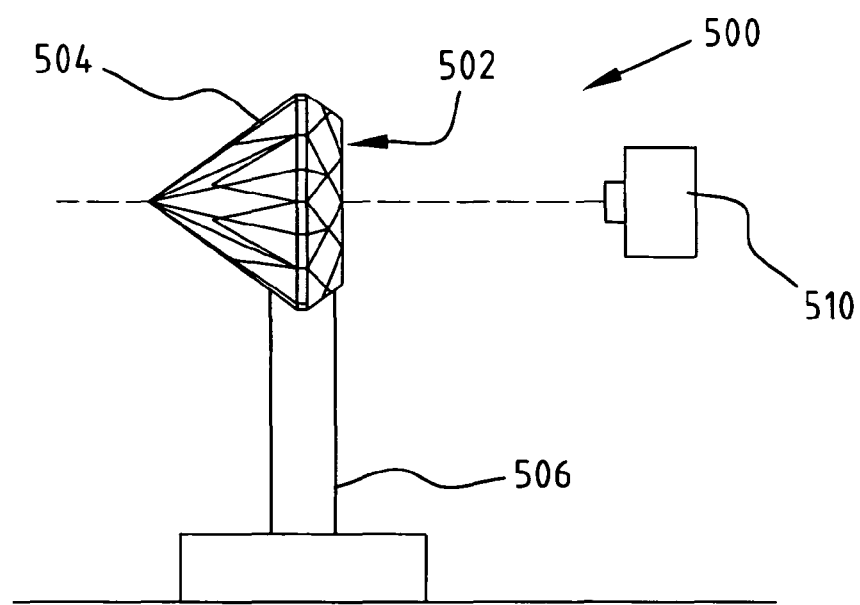
FIG. 5 is a schematic diagram showing a preferred arrangement for capturing images of a cut gemstone according to an embodiment of the present invention.

FIG. 5 is a schematic diagram showing a preferred arrangement 500 for capturing images of an ideal cut diamond 504, positioned on a holder 506, using an imaging device 510. The diamond 504 is arranged on the holder 506 such that the table 502 (ie the flat "top" surface of the cut diamond) may be oriented to face directly the imaging device 510. Such an arrangement is desirable, because the relatively large, flat table makes perpendicular image capture efficient, and also because this is the main viewing orientation used for viewing and clarity grading of the diamond 504.

It will be appreciated that other holding and supporting devices and/or arrangements for cut/polished gemstones also fall within the scope of the present invention. The most preferred holding apparatus minimises visual obstructions of a gemstone from all viewing directions, and ensures that optimal viewing orientations are available to the image capturing device (such as the arrangement 500 which enables the table 502 of an ideal cut diamond 504 to be oriented towards the imaging device 510). It is further preferred that as many degrees of freedom as possible be provided for rotation and/or translation of a gemstone relative to image capturing devices and/or lighting arrangements. However, as the exemplary embodiments described herein demonstrate, even a single axis of rotation, in combination with one, two, or three perpendicular axis of translation, may be sufficient for a useful implementation of the invention. Additionally, while the exemplary embodiments described and depicted herein assume, for simplicity, that the imaging device (eg cameras 110, 510), and lighting devices (eg 108) remain stationary, while the gemstone (eg 104, 504) is rotated and/or translated, it is only the orientation of the gemstone relative to the lighting and capturing devices that is relevant to the operation of embodiments of the invention. Accordingly, embodiments are envisaged in which imaging and/or lighting devices may be movable relative to the gemstone, or where multiple imaging and/or lighting devices may be provided for obtaining suitable images from different viewing positions.

It will be understood that the foregoing described embodiments of the invention are intended to be exemplary only, and should not be considered limiting of the scope of the invention, as defined in the following claims.

The invention claimed is:

1. A method of constructing a 3D virtual model of a gemstone including the steps of:
   performing measurements of the gemstone to construct a 3D virtual model of an exterior surface of the gemstone;
   identifying one or more visible inclusions within an interior volume of the gemstone;
   for each identified inclusion, performing the steps of:
      determining a location and 3D shape of the inclusion within the interior volume of the gemstone;
      capturing at least one image of the inclusion;
      using the at least one image to determine relevant optical characteristics of the inclusion;
   and
      constructing a 3D virtual model of the inclusion, said 3D virtual model of the inclusion including the 3D shape of the inclusion and optical properties of the inclusion based upon said optical characteristics;
   constructing a 3D virtual model of the gemstone, said 3D virtual model of the gemstone including the 3D virtual model of the exterior surface of the gemstone and the 3D virtual models of the one or more visible inclusions within the interior volume of the gemstone;
   generating a dataset representing said 3D virtual model of the gemstone; and
   using said dataset in subsequent computer analysis to provide a user with information relating to a visual characteristic of the gemstone;
   wherein the step of using the at least one image to determine relevant optical characteristics of the inclusion includes the sub-steps of:
   using the at least one image to assign an inclusion type to the inclusion; and
   on the basis of the assigned inclusion type, assigning optical characteristics to the inclusion, said optical characteristics being selected according to the inclusion type and properties of the inclusion observable in the at least one image;
   wherein the optical characteristics include at least one of reflectivity and transmittance.

2. The method of claim 1 wherein the gemstone is a rough stone,
   and the visual characteristic is a visual characteristic of a cut and/or polished gemstone proposed to be cut from the rough stone.

3. The method of claim 1, wherein using said dataset comprises generating and displaying a predicted photorealistic 3D image of the gemstone including the one or more inclusions, as viewed from a specified viewing position under specified lighting conditions, based on said dataset.

4. The method of claim 1 including the further step of computing and outputting a clarity grade of a cut and polished gemstone.

5. The method of claim 1 including the further step of computing and outputting a rating value relating to a visual performance criterion of a cut and polished gemstone, said visual performance criterion being selected from a list including: light return; contrast; brilliance; fire; and scintillation.

6. The method of claim 1 wherein the inclusion type assigned to each inclusion is selected from a list including: pinpoint; cloud; needle; and crack.

7. The method of claim 1 wherein the optical characteristics of each inclusion are represented in the 3D virtual model of the inclusion using one or more texture maps.

8. The method of claim 1 wherein the optical characteristics of each inclusion are represented in the 3D virtual model of the inclusion using one or more bidirectional reflectance distribution functions (BRDFs).

9. The method of claim 1, wherein said capturing at least one image comprises capturing multiple images under different predetermined lighting conditions;
   and said using the at least one image comprises using said multiple images to determine relevant optical characteristics of the inclusion.

10. A method of constructing a 3D virtual model of a gemstone including the steps of:
    performing measurements of the gemstone to construct a 3D virtual model of an exterior surface of the gemstone;
    identifying one or more visible inclusions within an interior volume of the gemstone;
    for each identified inclusion, performing the steps of:
       determining a location and 3D shape of the inclusion within the interior volume of the gemstone;
       capturing at least one image of the inclusion;
       using the at least one image to determine relevant optical characteristics of the inclusion;
    and
       constructing a 3D virtual model of the inclusion, said 3D virtual model of the inclusion including the 3D shape of the inclusion and optical properties of the inclusion based upon said optical characteristics;
    constructing a 3D virtual model of the gemstone, said 3D virtual model of the gemstone including the 3D virtual model of the exterior surface of the gemstone and the 3D virtual models of the one or more visible inclusions within the interior volume of the gemstone;
    generating a dataset representing said 3D virtual model of the gemstone; and
    using said dataset in subsequent computer analysis to provide a user with information relating to a visual characteristic of the gemstone; wherein said at least one image of an inclusion comprises a plurality of images of the inclusion captured from different relative viewpoints, and wherein the method includes the steps of:
    using said plurality of images to determine relevant optical characteristics of the inclusion as viewed from the different relative viewpoints; and
    combining the optical characteristics in constructing a 3D virtual model of the inclusion.

11. The method of claim 10 wherein the step of capturing at least one image of each inclusion is performed under predetermined lighting conditions, and wherein the step of determining relevant optical characteristics of each inclusion uses a ray-tracing process including the steps of:
    reproducing the predetermined lighting conditions in a computer-generated virtual environment including a 3D virtual model of the inclusion having estimated optical characteristics;

generating at least one virtual image of the inclusion corresponding with the captured at least one image of the inclusion;

comparing the at least one virtual image with the captured at least one image; and if the at least one virtual image does not match the captured at least one image, then modifying the estimated optical characteristics of the 3D virtual model of the inclusion and repeating the generating and comparing steps.

12. The method of claim 10, further comprising: generating a photorealistic 3D image of the gemstone using said data set and taking into account viewing optics.

13. An apparatus for constructing a 3D virtual model of a gemstone, including:
   a gemstone measurer that obtains measurements of the gemstone to construct a 3D virtual model of an exterior surface of the gemstone:
   a visible inclusion identifier to identify one or more inclusions within an interior volume of the gemstone;
   an inclusion 3D virtual model constructor to construct a 3D virtual model of each identified inclusion;
   a gemstone 3D virtual model constructor to construct a 3D virtual model of the gemstone including the 3D virtual model of the exterior surface of the gemstone and the 3D virtual models of the one or more visible inclusions within the interior volume of the gemstone; and
   a dataset generator for generating a dataset representing said 3D virtual model of the gemstone,
   wherein said dataset may be used in subsequent computer analysis to provide the user with
   information relating to a visual characteristic of the gemstone, and
   wherein the inclusion 3D virtual model constructor includes:
      image capturer for capturing at least one image of the inclusion;
      a determining component for using the at least one image to determine relevant optical characteristics of the inclusion; and
      a 3D virtual model constructor for constructing a 3D virtual model of the inclusion, said 3D virtual model of the inclusion including the 3D shape of the inclusion and optical properties of the inclusion based upon said optical characteristics; wherein the determining component for using the at least one image to determine relevant optical characteristics of the inclusion includes:
      an assignor for using the at least one image to assign an inclusion type to the inclusion; and
      a responder responsive to the assigned inclusion type which assign zero or more further characteristics to the inclusion, said further characteristics being selected according to the inclusion type and properties of the inclusion observable in the at least one image.

14. The apparatus of claim 13 including a generator for generating and
   displaying a predicted visual appearance of the gemstone as viewed from a specified viewing position under specified lighting conditions.

15. The apparatus of claim 13 including a module for computing and outputting a clarity grade of a cut and polished gemstone.

16. A system for constructing a 3D virtual model of a gemstone, including:
   a gemstone scanning apparatus configured to perform measurements of the gemstone to
   construct a 3D virtual model of an external surface of the gemstone;
   a computer having at least one central processor, a display device, and one or more user input devices, the computer being operatively connected to the scanning apparatus and configured to receive information from the scanning apparatus defining an exterior surface of the gemstone;
   the computer further including at least one non-transitory storage medium operatively associated with the
   processor and containing instructions executable by the processor for performing the steps of:
      identifying one or more visible inclusions within an interior volume of the gemstone;
      for each identified inclusion, constructing a 3D virtual model of the inclusion;
      constructing a 3D virtual model of the gemstone including the 3D virtual model of the exterior surface of the gemstone and the 3D virtual models of the one or more visible inclusions within the interior volume of the gemstone; and
      generating and storing within the non-transitory storage medium a dataset representing said 3D virtual model of the gemstone,
   wherein said dataset may be used in subsequent computer analysis to provide a user with
   information relating to a visual characteristic of the gemstone, and
   wherein the instructions executable by the processor for performing the step of constructing a 3D virtual model of each inclusion include instructions executable by the processor for performing the substeps of:
      capturing at least one image of the inclusion;
      using the at least one image to determine relevant optical characteristics of the inclusion;
   and
   constructing a 3D virtual model of the inclusion, said 3D virtual model of the inclusion including the 3D shape of the inclusion and optical properties of the inclusion based upon said optical characteristics; wherein the instructions executable by the processor for performing the sub-step of using the at least one image to determine relevant optical characteristics of the inclusion include instructions for performing the further sub-steps of:
   using the at least one image to assign an inclusion type to the inclusion; and
   on the basis of the assigned inclusion type, assigning zero or more further characteristics to the inclusion, said further characteristics being selected according to the inclusion type and properties of the inclusion observable in the at least one image.

17. The system of claim 16 wherein the non-transitory storage medium further contains instructions executable by the processor to display captured images to the user on the display device, and to generate and display photorealistic 3D virtual images of the gemstone on the display device based on said data set.

* * * * *